US006824511B1

(12) United States Patent
Bell et al.

(10) Patent No.: US 6,824,511 B1
(45) Date of Patent: Nov. 30, 2004

(54) SURGICAL FIXATION AND RETRACTION SYSTEM

(75) Inventors: Michael S. G. Bell, Ottawa (CA);
Leonard G. Lee, Almonte (CA);
Michael T. O'Malley, Appleton (CA);
Timothy J. Maxwell, Kanata (CA)

(73) Assignee: Canica Design Inc., Almonte (CA)

( * ) Notice: Subject to any disclaimer, the term of this patent is extended or adjusted under 35 U.S.C. 154(b) by 0 days.

(21) Appl. No.: 09/857,246

(22) PCT Filed: Dec. 1, 1999

(86) PCT No.: PCT/IB99/01927

§ 371 (c)(1),
(2), (4) Date: Aug. 31, 2001

(87) PCT Pub. No.: WO00/32111

PCT Pub. Date: Jun. 8, 2000

Related U.S. Application Data

(60) Provisional application No. 60/140,583, filed on Jun. 23, 1999.

(51) Int. Cl.[7] .................................................. A61B 1/32
(52) U.S. Cl. ....................................................... 600/227
(58) Field of Search ............................... 600/226, 227, 600/231, 232, 233, 234, 1

(56) References Cited

U.S. PATENT DOCUMENTS 2,586,488 A * 2/1952 Smith .......................... 600/234
2,845,925 A 8/1958 Jayle (List continued on next page.)

FOREIGN PATENT DOCUMENTS

| EP | 0279534 A | 8/1988 |
|---|---|---|
| EP | 0792622 A1 | 9/1997 |
| GB | 328741 | 5/1930 |
| WO | WO 96/10954 A | 4/1996 |
| WO | WO 99/05973 A | 2/1999 |
| WO | WO 99/35974 A | 7/1999 |
| WO | WO 00/10466 A | 3/2000 |
| WO | WO 00/32111 A | 6/2000 |
| WO | WO 01/85035 A | 11/2001 |

OTHER PUBLICATIONS

Abstract—Pavletic, M.M., "Use of an External Skin–Stretching Device for Wound Closure in Dogs and Cats", J. Am. Vet. Med. Assoc., Aug. 1, 2000, 217 (3): 350–354.
Abstract—Ritzman, T.K., "Use of an External Skin Stretching Device in a Guinea Pig", Exotic DVM, Jan. 2001, 3 (1): 31–35.
PCT International Search Report; PCT/IB 02/03037.

*Primary Examiner*—Cary E. O'Connor
(74) *Attorney, Agent, or Firm*—Kilpatrick Stockton LLP; John S. Pratt; Camilla C. Williams

(57) ABSTRACT

A fixation and retraction system utilizing base components to which shielded magnet components attach in order to locate movable fixation and retraction components or other operating theater devices, such as surgical drapes. Use of rare earth magnets permits system components to be attached quickly, easily and securely in almost an infinite number of configurations.

104 Claims, 11 Drawing Sheets

U.S. PATENT DOCUMENTS

| | | | | |
|---|---|---|---|---|
| 3,698,395 | A | 10/1972 | Hasson | |
| 3,762,401 | A | 10/1973 | Tupper | |
| 3,823,709 | A | 7/1974 | McGuire | |
| 3,976,079 | A | 8/1976 | Samuels et al. | |
| 4,430,991 | A * | 2/1984 | Darnell | |
| 4,693,236 | A * | 9/1987 | Leprevost | |
| 5,013,243 | A * | 5/1991 | Tanaka et al. | 433/189 |
| 5,123,843 | A * | 6/1992 | Van der Zel et al. | 433/189 |
| 5,234,462 | A | 8/1993 | Pavletic | |
| 5,263,971 | A | 11/1993 | Hirshowitz et al. | |
| 5,384,103 | A * | 1/1995 | Miller | 422/310 |
| 5,507,775 | A | 4/1996 | Ger et al. | |
| 5,580,344 | A | 12/1996 | Hasson | |
| 5,649,960 | A | 7/1997 | Pavletic | |
| 5,665,108 | A | 9/1997 | Galindo | |
| 5,871,357 | A * | 2/1999 | Tseng | 433/189 |
| 5,876,333 | A | 3/1999 | Bigliani et al. | |
| 6,102,854 | A * | 8/2000 | Cartier et al. | 600/228 |
| 6,190,312 | B1 | 2/2001 | Fowler, Jr. | |
| 6,478,656 | B1 | 11/2002 | Khouri | |
| 6,517,563 | B1 * | 2/2003 | Paolitto et al. | 600/206 |

* cited by examiner

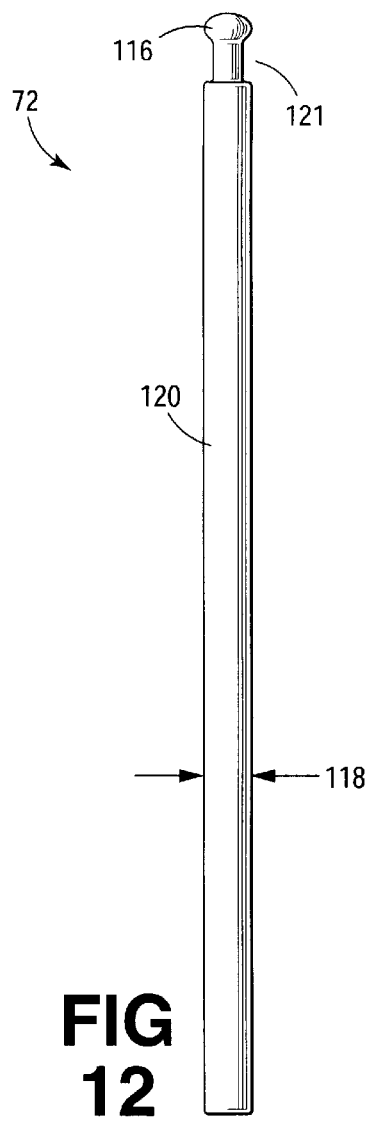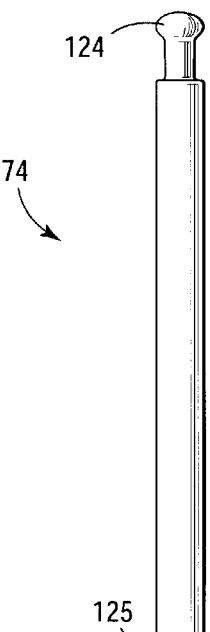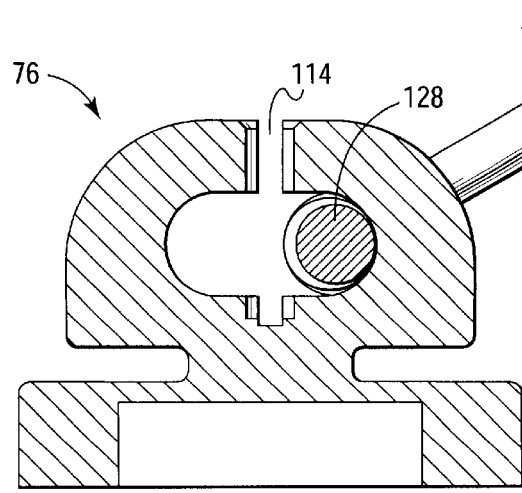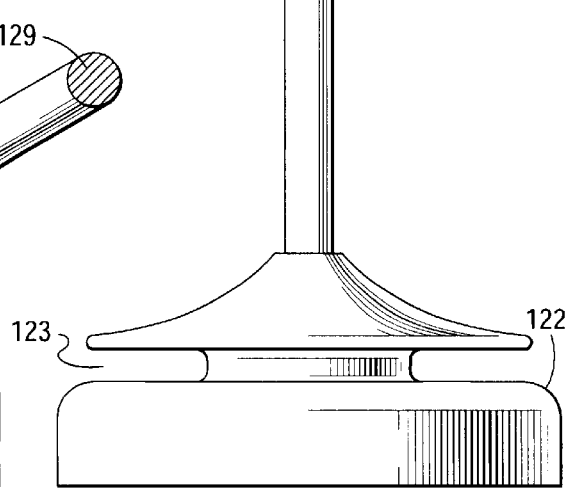
FIG 12
FIG 11
FIG 13

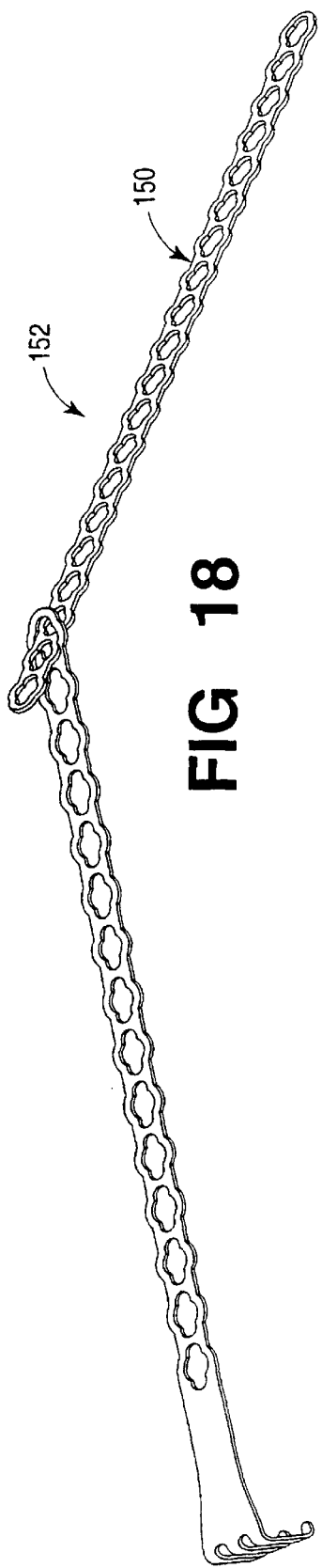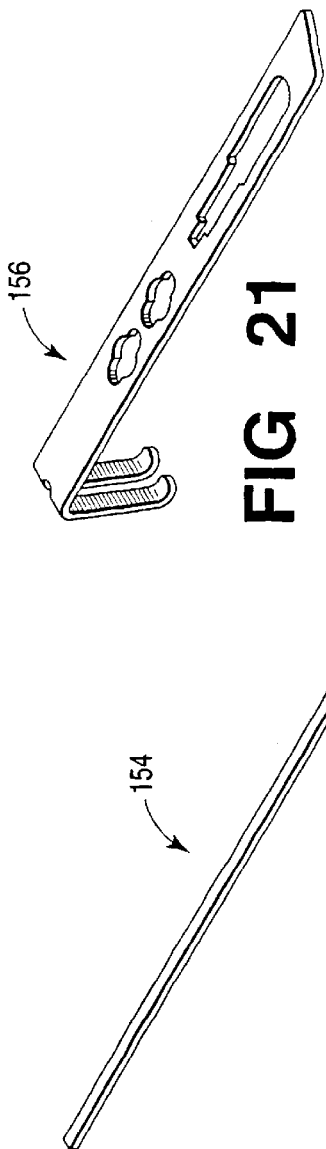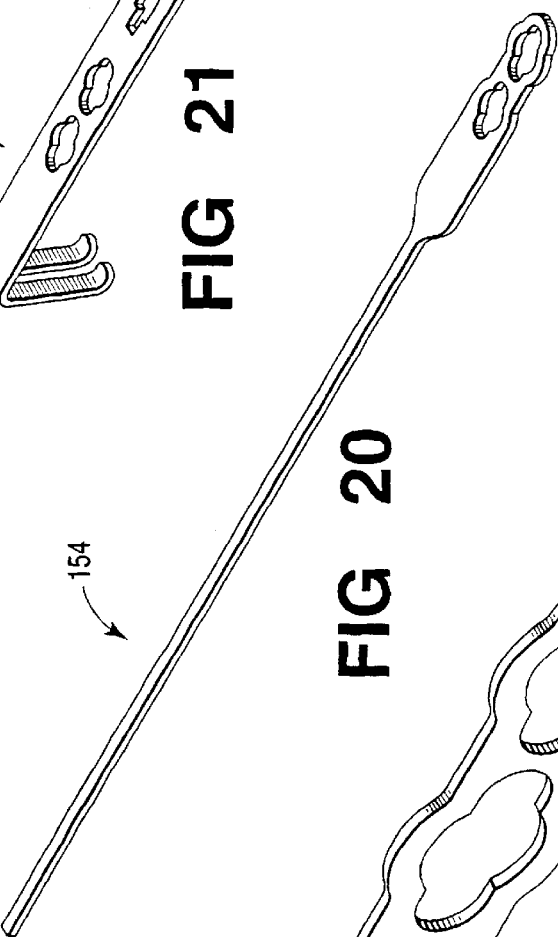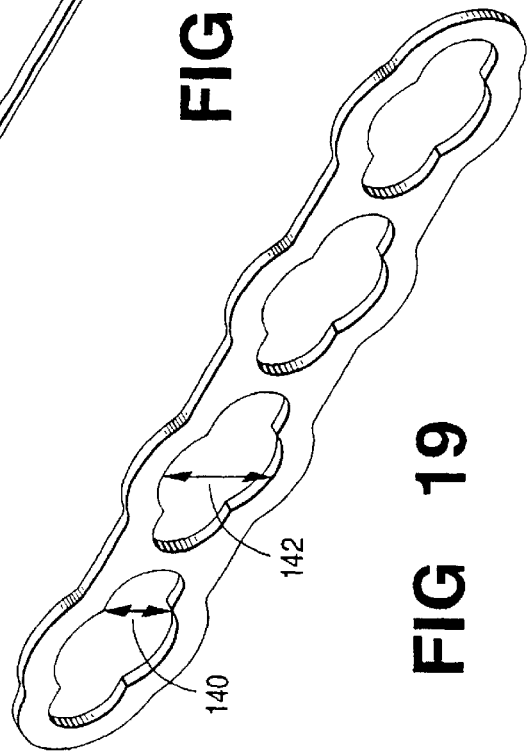

SURGICAL FIXATION AND RETRACTION SYSTEM

This application claims the benefit of Provisional Application No. 60/140,583 filed Jun. 23, 1999.

BACKGROUND

1. Field of the Invention

This invention relates to systems and methods for fixation or immobilization and retraction of various anatomical and other structures during surgery, including, for example, surgical fixation and retraction of flesh, bone, feet, legs, arms, hands, digits, surgical drapes, and other surgical equipment.

2. Prior Art

Although elements of many new technologies have been transferred to medicine from their original fields, this has generally not happened in the area of basic surgical instruments, even though surgery still largely depends on the skill of an individual surgeon using these tools. Recent research and development activity in medical equipment has been more focused on expensive procedure sets, diagnostic tools, and life-support systems. As a result, conventional surgical fixation and retraction devices have changed slowly and suffer from a number of shortcomings.

(a) Retraction

Surgical retractors are used to provide medical personnel with the ability to hold open an incision area. Typically, retractors are band held or mount on a fixed support assembly. Restraining limbs and digits provides a particular challenge for medical personnel. Hand surgery requires a retraction system that provides a surgeon with flexibility and stability. For example, a surgeon may wish to stabilize a wrist or forearm while adjusting retractors around an incision area of a hand or finger. Often critical decisions are made during the course of the surgical procedure that require alteration to the fixation apparatus.

Traditional retraction systems typically utilize mechanical fasteners to provide a rigid connection among components. Re-positioning the retractor may require additional equipment to change retractive or stabilizing forces. Additional tools may also be required to assemble or to disassemble equipment. This presents problems because it is difficult to add or change equipment in an operating room without compromising the sterile environment. As a result, surgical procedures can be delayed while additional sterile equipment is introduced to the operating facility.

(b) Fixation

A variety of needs also arise in connection with surgery to fix the position of structures, such as surgical instruments, drapes, or a portion of a patient's anatomy, some of which structures "resist" repositioning or maintenance of a selected position. These needs are conventionally addressed with adhesive, such as by use of adhesive tape, and by use of devices that mechanically connect or attach, such as clamps and retractors.

Another problematic shortcoming of existing fixation systems is their reliance on threaded or incremental adjusters. Threaded adjusters are frequently too slow for midprocedure adjustment. Incremental adjusters are faster but often exert too little or too much retraction in detent positions.

Advances in surgical techniques have created the need for a fixation and retraction system that can be manipulated by the surgeon in the course of the procedure. This is often necessary to provide clear and varied views (visualization) of the incision site during the procedure. Traditional systems and practices require the presence of an assistant for the duration of the procedure to provide and adjust retraction. As a result, procedure errors can occur because of misunderstood verbal communication between the surgeon and the assistant. Thus, it is desirable for the surgeon to be able to manipulate the apparatus and is preferable that it be possible to do so with one hand.

(c) Drapes

Surgical drapes cover patients during surgery to maintain a sterile environment around the operative site. Traditional drapes consisted of cotton polyester blend textile similar to bedsheets. Users of this traditional fabric encounter problems of poor fluid transmission control and virtually no containment of fluids.

In a traditional drape fixation system, pincer style towel clips grasp a surgical drape and are secured to a patient or operating room structure with adhesive tape. To cover a patient with a surgical drape during a surgical procedure using the traditional fixation system, a user must lay a drape over the patient. Once in position, the user clasps a portion of the drape with the pincers of a towel clip. Pincers have pointed tips requiring care by users to avoid puncturing the drape. After grasping the drape, the user must secure the towel clip to a surface, such as an operating room table. Typically, adhesive tape is placed through a towel clip loop and affixed to a surface. In some situations, drapes must be clipped or sutured to the patient to provide fail-safe protection.

New drape fabrics have been developed, including one introduced by W. L. Gore using Goretex™ fabric. Use of the Goretex™ drape during a surgical procedure offers advantages found in outdoor clothing such as protection against wetness. However, new problems are associated with use of the Goretex™ drape. Holes in the drape resulting from the pincer style towel clips destroy the desirable properties of the membrane. It is also undesirable to puncture such drape material with sutures.

In response to these problems, a new generation of drape clips have locking hemostats with large blunt surfaces to support the drape material. In addition, double faced tapes are available for securing drapes. However, double faced adhesive tapes lack the ability to adhere to the drapes effectively, particularly when attaching drapes to skin. This problem has led to somewhat extreme procedures such as scrubbing the patent to improve adhesion. Thus, current fastening methods are inefficient and unreliable, and a need exists for a method and system for securing a surgical drape to a skin surface without puncturing the surgical drape.

The above-described needs and problems, which are merely exemplary, demonstrate that a need exists for a surgical fixation and retraction system that provides stability while allowing efficient, sterile, relatively effortless adjustment of the system prior to or during a surgical procedure.

SUMMARY OF THE INVENTION

This system utilizes table-like ferromagnetic, typically metal, base components to which shielded magnet components attach in order to locate movable fixation and retraction components or other operating theater devices, such a surgical drapes. Ferromagnetic material conducts magnetic flux lines and is therefore attracted to, and attracts, magnets. Use of small, powerful rare earth magnets permits system components to be attached quickly, easily and securely in an almost infinite number of configurations.

Several different configurations of magnet-containing components are designed for direct contact with anatomical and other structures and for attachment to elastic and metal fixation and retraction components. Many of the magnet-containing components resemble chess pieces and are symmetrical about a longitudinal axis normal to the face of the magnet that attaches the component to a metal plate that serves as the base component. As a result, only location on the base plate matters, while rotational position relative to the base plate and other components does not matter. This simplifies assembly and adjustment of the components during use since rotational position generally does not need to be controlled. Fixation components in the form of such bodies of rotation are readily manufactured and are also well adapted for use with readily available disc-shaped rare earth magnets. These shapes also facilitate magnetic flux management, which is critical in the& operating theater environment where numerous ferromagnetic components and sensitive instrumentation may be present.

As is demonstrated in the detailed description of illustrative embodiments of the invention and some of the accompanying figures, this invention is readily usable for human hand surgery. It may also be used in a variety of other human and veterinary surgical procedures with appropriate adjustment of the scale of the components to match the requirements of the, human or animal anatomy involved.

The system is also usable for fixation of a surgical drape. One surgical drape fixation embodiment uses a metal cup and fixation tape to secure a surgical drape to a skin surface by attaching one magnet-containing structure to a skin surface with adhesive tape and trapping the drape between the magnet-containing structure and a second magnet or other component attracted by the magnet-containing structure. The metal cup includes a rim for coupling to the fixation tape, and the second side has a recess that receives one of the magnets. Two-sided adhesive tape bonds the cup to a skin surface or other surface. This embodiment gives medical personnel the ability to secure a surgical drape to the sterilized components of the fixation and retraction system while providing flexibility to adjust the position of the drape as needed. Securing a surgical drape with this invention protects a patient from fluid or other contaminants during a surgical procedure.

The fixation and retraction system of this invention reduces preparation and setup time, providing superior control and visualization and resulting in significantly reduced procedure times. The system provides a new level of direct control minimizing error from miscommunication between surgeon and assistant using powerful permanent rare-earth magnets. Force can be exerted and objects may be adjustably positioned during surgery using magnetic components, permitting a broad range of applications and component interoperability.

Use of rare-earth magnets in medical applications is challenging. The magnets must able to withstand autoclave temperatures and vigorous cleaning systems without power loss. Rare earth magnets contain iron, which requires corrosion protection. Normal magnet plating will not withstand repeated cleaning cycles, and encapsulation degrades magnetic performance. At the same time, the magnetic strength has to be harnessed in a manner that captures the bipolar power while controlling the magnetic flux field. The temperature, cleaning, corrosion and flux management problems can be solved by utilizing a magnetic alloy that is unaffected by temperatures up to 300° Fahrenheit (150° Celsius), and by creating thin wall stainless steel containers that hermetically seal the magnet and by fully shielding the magnets. At the same time, the system fixation components are designed to focus their magnetic strength on a single face, harnessing the maximum power of the magnets while simultaneously controlling the flux fields.

Unshielded magnets display a natural magnetic field consisting of a series of polar radiating loops of flux lines. In an unshielded state, magnets attract equally at their north and south poles. Once established on a metal plane, such an unshielded magnet provides both fixative force to the plate as well as radiating attractive force from the unobstructed pole, which is amplified from the natural state due to decrease in flux path losses. In a surgical environment, radiating magnet flux attracts all ferromagnetic materials, which can be undesirable. Flux management therefore can be an important feature of the system. Since a variety of ferromagnetic components are used during many surgical procedures, it is important that there are very high attractive forces between the components and the base plate and that the attractive force upward is minimized.

Shielded magnets allow for optimal utilization of the magnetic attractive forces and minimize the undesirable radiation of magnetic flux. For example, disk magnets have equal fields on each side of the disk. When a disk magnet is placed in a ferromagnetic cup, the cup magnifies the fixative force at the mouth of the cup by eliminating the air gap (air is a poor conductor of magnetic fields) and brings both poles of the magnet to grip on the plate surface. A secondary effect is substantial reduction of radiated magnetic flux. A magnet held in a ferromagnetic fixture provides an increase in fixation strength through field focus over a bare magnet while magnetic shielding is provided through a closed magnetic loop.

Autoclavable magnets include rare earth magnets such as the Somarium Cobalt (SmCo) types or formulations including neodymium, iron, and boron for coercivity retention at high temperatures like those in an autoclave. Other magnets that provide magnetic properties adequate for the application and that can be sterilized are also usable. Additionally, computer controlled laser welding permits the creation of thin wall stainless steel containers that hermetically seal the magnet, preventing corrosion without materially degrading the magnetic circuit performance.

One advantage of this surgical system is unrestricted motion, providing ease in positioning components. The magnetic fixators can be anchored anywhere on the surgical table, yet only two fingers are required for repositioning or fine tension control. The forces of magnetic attraction and tabletop friction are balanced to create an intuitively tactile holding system.

Surgeons often rely on the steady hand of a skilled assistant to follow their every move or command throughout a surgical procedure. This system reduces the surgeon's dependency on a helping hand by providing control of fixation and retraction. The components often can be set, released, and manipulated with one or two fingers. An advantage to this system is that in many cases the surgeon can conduct the procedures without assistance, permitting some procedures to be carried out in a clinical setting under local anesthetic, rather than in a standard operating room.

Retraction applied by the surgeon is precisely maintained by the system. In a hand surgery embodiment, the system provides either static or dynamic forces up to about 800 grams. The 360° radial retraction and slim retractor profiles improve visualization at the operative site. All of the components snap or slide together, allowing the surgeon to create and evolve fixation and retraction solutions as required throughout a procedure. The use of magnets provides properties not available with purely mechanical devices. The ability to move and leave a component under tension :using a contained but powerful built-in magnetic field avoids the use of locking or latching mechanisms common to purely mechanical systems. The system is not only faster, but also provides a far more sensitive adjustment range. The system uses strong rare-earth magnets built into component bases with a design that maximized fixative properties while effectively containing magnetic flux fields.

This fixation and retraction system stabilizes structures during surgery while allowing efficient, sterile adjustment of the system prior to or during a surgical procedure. The system may be used during various types of surgical procedures, including, but not limited to, hand, limb, digits, crania-facial, and veterinary surgery.

In one embodiment, this invention is a system for using a magnet in surgical fixation. In one form of this embodiment, the magnet forms part of a fixation component, which may also include a non-magnetic housing and a ferromagnetic cup. Another form of this embodiment includes a fixation component containing the magnet, and a ferromagnetic base plate to which the magnet attaches. In yet another form, the fixation component includes the magnet, a housing for the magnet, and a cleat attached to the housing.

Another embodiment of the invention is a device for repositionably securing a structure in a desired position during surgery, which device contains a magnet. One form of this embodiment can include a fixation component, a coupling component, a silicone rubber tube and a ferromagnetic base plate.

Yet another embodiment of this invention is a method for stabilizing or retracting an anatomical member during surgery that involves coupling a magnet to the anatomical member and attaching the magnet to a ferromagnetic base plate.

Accordingly, one feature of this invention is a surgical fixation and retraction system using magnetic components.

A further feature of this invention is a fixation and retraction system that allows good visibility of the operative site.

Another feature of this invention is a fixation and retraction system that provides a rigid connection and that has components that are part of a system and that are compatible with all other system elements.

An additional feature of this invention is that the components of the system disassemble for easy sterilization or disposal. Further, components do not degrade during aggressive sterilization methods.

Another feature of this invention is support on multiple planes. The system of this invention provides a broad range of retractive or stabilizing forces.

Another feature of this invention is very precise stabilization without backlash. Multiple components combine in series to increase range or in parallel to increase strength.

An additional feature of this invention is that no tools are required to set up or disassemble the surgical fixation and retraction system.

Another feature of this invention is to provide an invention that adapts to include non-system components.

Another feature of this invention is management of the collective magnetic forces generated by the system so as not to create undesirable magnetic attraction.

A feature of this invention is a surgical fixation and retraction system using magnets to hold through drape material without puncturing the membrane of the material.

An additional feature of this invention is a surgical fixation and retraction system with system components that operate through sterile drapes or plastic film without damage and provide isolation from other medical apparatus while maintaining stabilization.

Another feature of this invention is a method and system for attaching a surgical drape to a skin surface.

These and other features of this invention will be readily understood by those skilled in the art by reference to the following descriptions of the invention and the accompanying drawings.

BRIEF DESCRIPTION OF THE DRAWINGS

FIG. 11 is a cross sectional view through the vertical center of the cam locking base of this invention.

FIG. 12 is a side elevation view of the lance of this invention.

FIG. 13 is a side elevation view of the knight of this invention.

FIG. 18 is a perspective view of the extension retraction component of this invention joined with another retraction component of this invention.

FIG. 19 is a perspective view of a retractor extension end of this invention.

FIG. 20 is a perspective view of a specialty retractive component of this invention.

FIG. 21 a perspective view of a scalpel holder of this invention.

DETAILED DESCRIPTION OF SPECIFIC EMBODIMENTS

Overview

Figure 1:
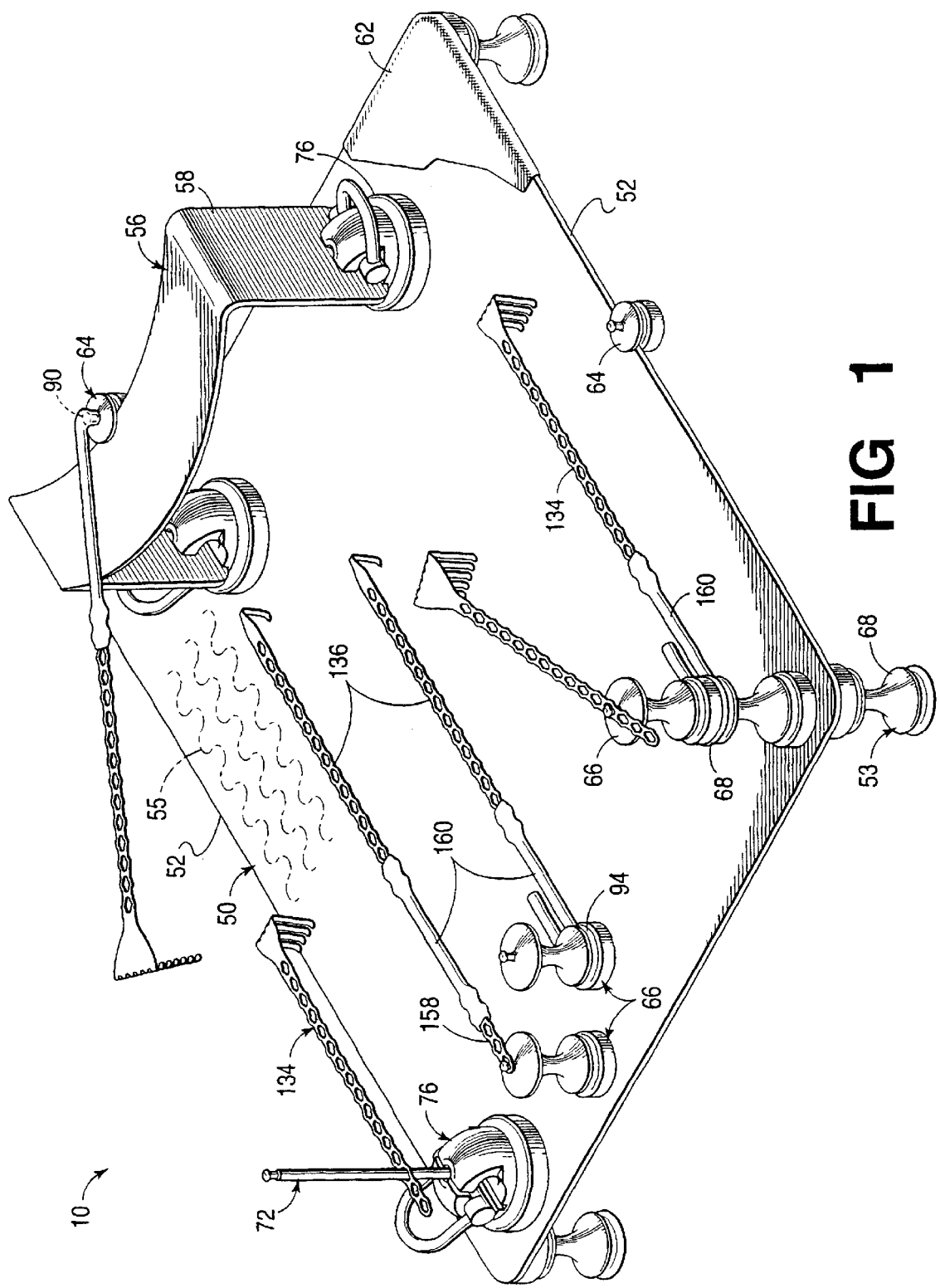
FIG. 1 is a perspective view of various components of the fixation and retraction system of this invention.
Figure 2:
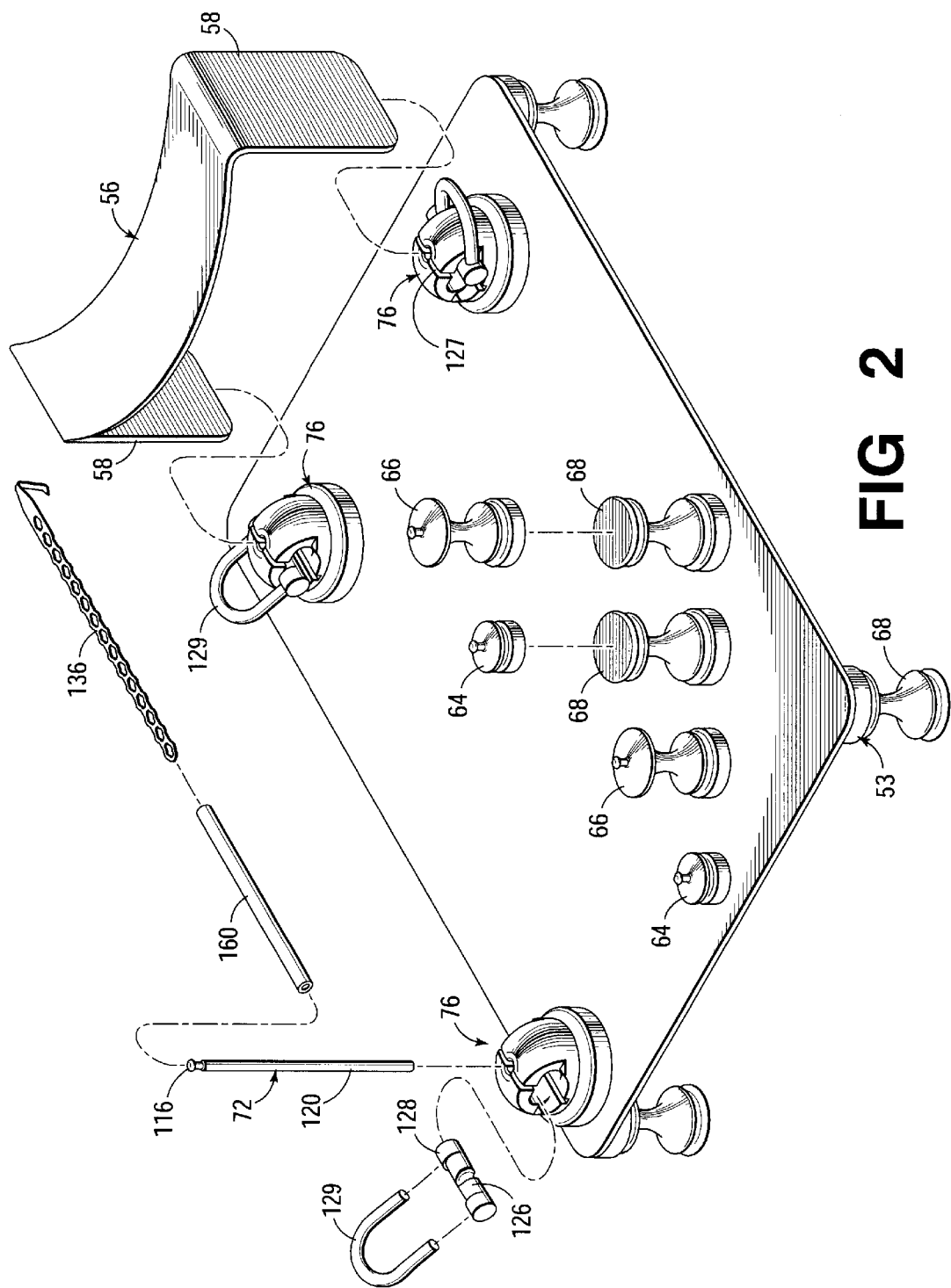
FIG. 2 is an exploded perspective view of various components of the fixation and retraction system.
Figure 3:
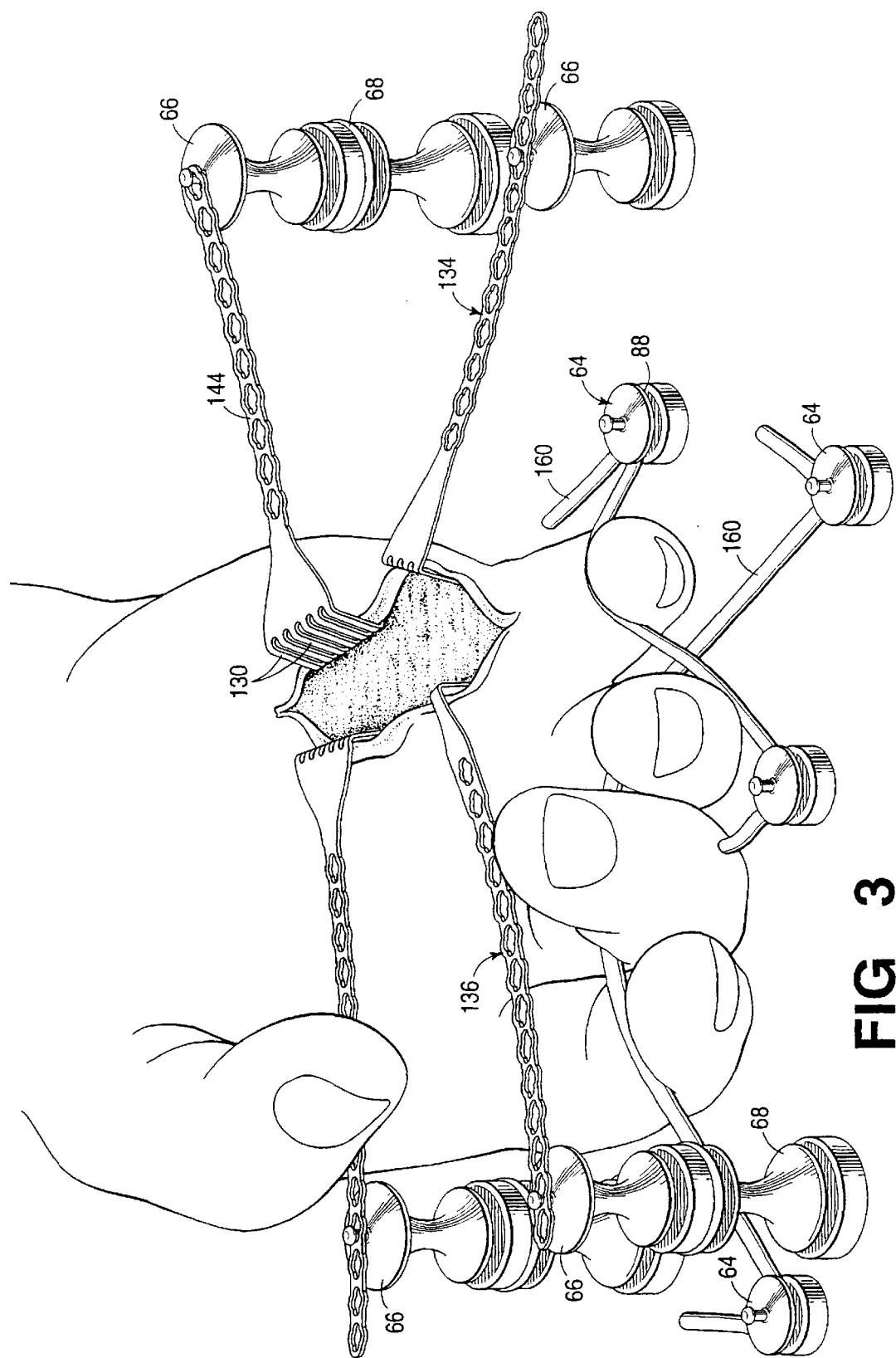
FIG. 3 is a perspective view of various components of the fixation and retraction system of this invention used during hand surgery.
Figure 23:
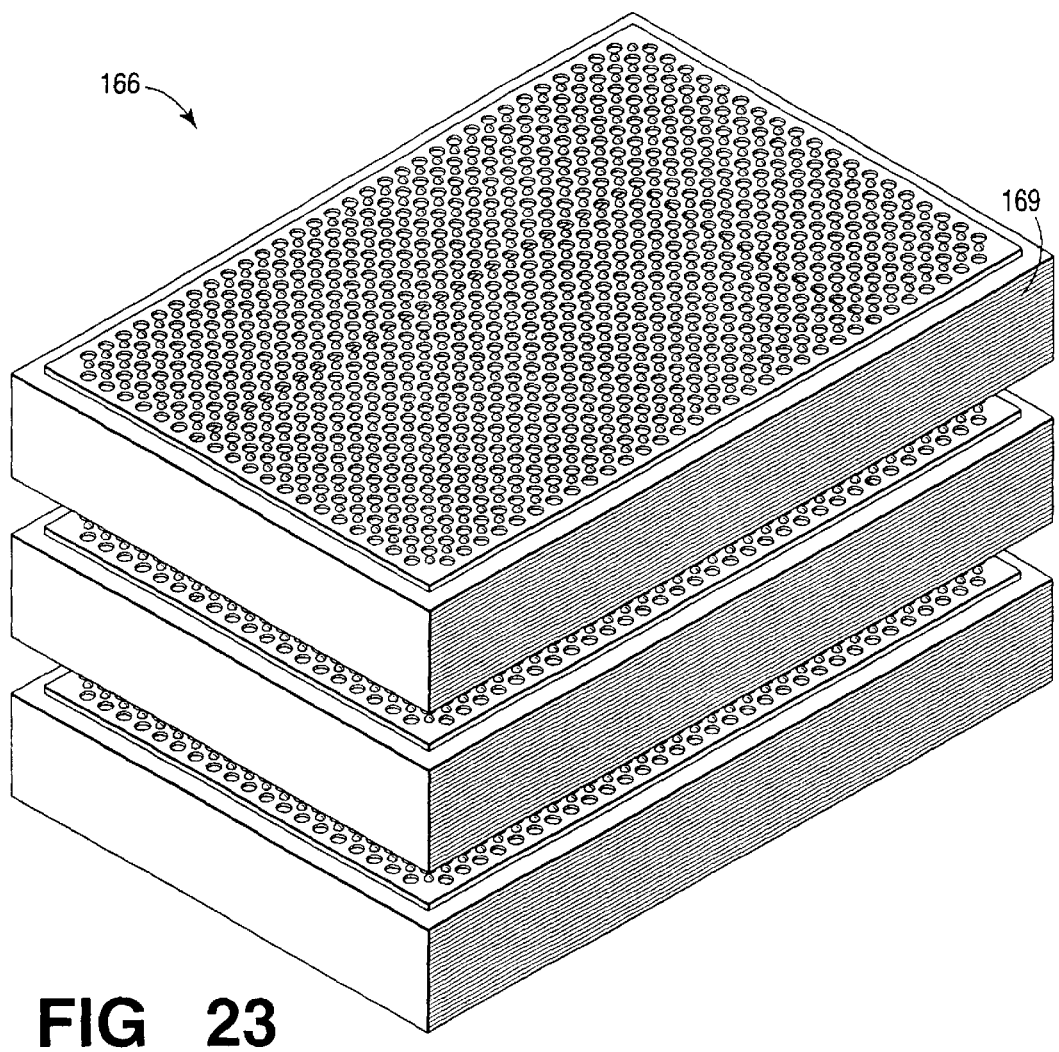
FIG. 23 is an exploded perspective view of stacked sterilization trays of this invention.
Figures 24, 25, 26:
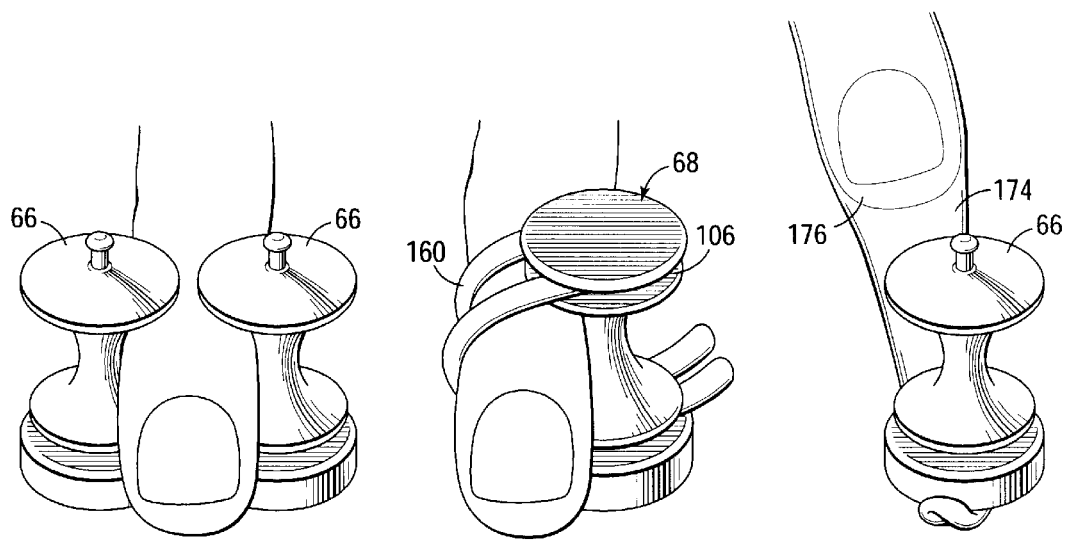
FIG. 24 is a perspective view of a method of fixation using this invention to trap and stabilize digits.
FIG. 25 is a perspective view of a method of fixation using this invention to bind digits.
FIG. 26 is a perspective view of a method of fixation using this invention to stabilize a gloved finger.

This fixation and retraction system 10 may be utilized during a surgical procedure to stabilize, immobilize, or retract structures such as, but not limited to, flesh, bone, feet, legs, arms, hands, digits, surgical drapes, and other surgical equipment. The system 10 generally includes table components, fixation components, retraction components, and dynamic components. Various components are used for coupling a magnet to anatomical members or other surgical theater devices such as surgical drapes. FIG. 1 illustrates possible combinations of the components of the system to form a variety of magnetic and mechanical structures. FIG. 2 shows discreet components as an exploded perspective view. FIG. 3 shows various components of the system, as used during a surgical procedure of the hand. FIGS. 4–23 illustrate individual components of the system in more detail, while FIGS. 24–26 show additional combinations. FIGS. 27–30 show alternative embodiments of the system for use in securing surgical drapes during surgery.

Table Components

Figure 4:
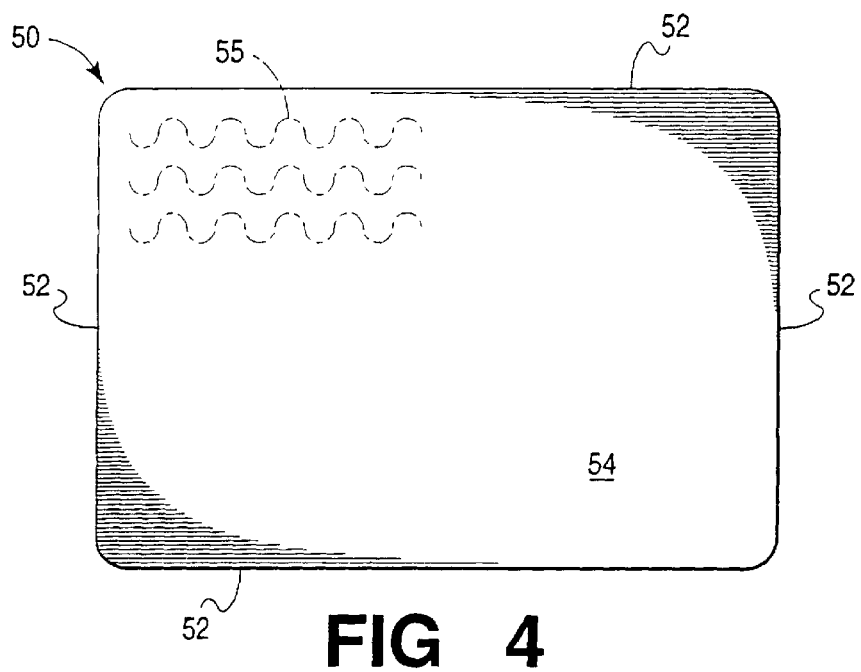
FIG. 4 is a top plan view of the plate of the fixation and retraction system of this invention.

The foundation of the table components is stainless-steel plate 50, which is essentially the surgical operating table or base, as shown in FIG. 1. Plate 50 may be formed from 0.065 inch thick stainless steel. As shown in FIGS. 1, 2, and 4, plate 50 has four edges 52 and stainless steel surface 54. In one embodiment, plate 50 has four feet 53, shown in FIGS. 1 and 2. One or both faces of plate 50 may be laser etched or otherwise permanently marked with text or diagrams 55 so that it is a complete instructional tablet. This is advantageous because traditional paper instructions tend to be lost, so that advanced functionality is forgotten and therefore effectively lost over time.

Figure 5:
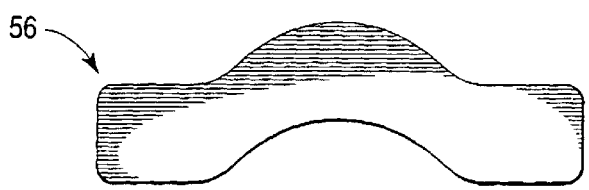
FIG. 5 is a top plan view of the wrist bridge of the fixation and retraction system of this invention.
Figure 6:
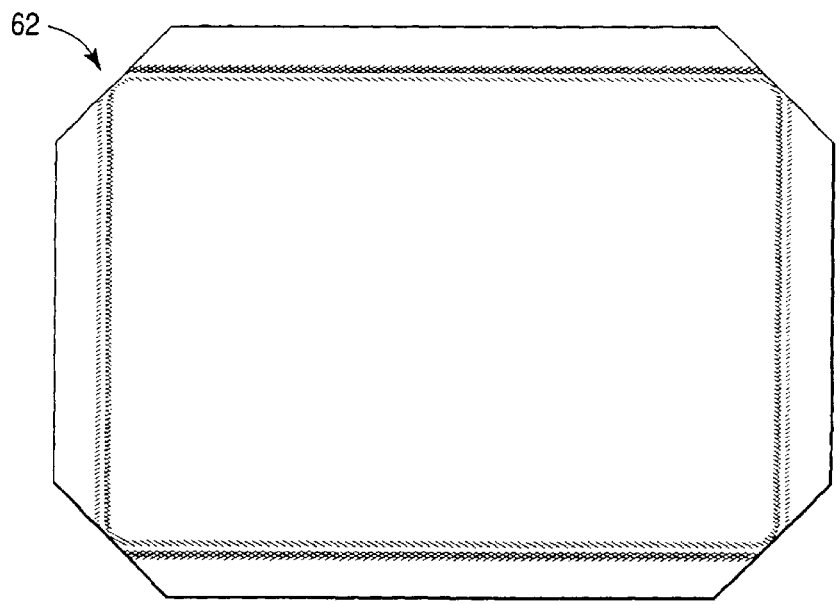
FIG. 6 is a top plan view of the fabric plate cover of this invention.

Bridge 56, shown in FIGS. 1, 2, and 5, is a crescent-shaped plate which, as its name implies, bridges a body part, such as the wrist, and serves as an auxiliary base. Bridge 56 may be held in place by fixation components called "cam locking bases," discussed below. Bridge 56 has legs 58, formed, as can be seen in FIG. 2 by bending each end of stainless steel bridge plate 56 at a 90° angle to the rest of the bridge 56. Bridge 56 provides an anchor for retraction components at an elevated height in the area where part of the body, such as the wrist and forearm, cover base plate 50. Bridge 56 may be custom made in any size or shape. Adding bridge 56 allows the system to provide retraction at any vector above the base plate 50, permitting retraction toward any point in a hemisphere covering the surgical field. This is ideal for palm or wrist procedures requiring proximal reaction. Bridge 56 has the same ferromagnetic properties as plate 50, and all of the fixation components can be used with it. Bridges 56 can be combined to build semi-circular or circular structures.

As shown in FIGS. 1 and 2, plate 50 may be covered with microfiber textile surgical fabric 62 or used bare. In one embodiment, fabric 62 has an octagonal shape, formed by removing corner portions of a rectangle, shown in FIG. 6. Fabric 62 aids in movement of the fixation components on plate 50 by decreasing the coefficient of friction. Thus, through their functional range, stationary to full motion, the fixation components provide near linear resistance. This permits the surgeon to make fine adjustments using one finger to slide the fixation components along the operating surface with a linear and predictable force. At rest, a fixation component indents fabric 62 slightly so that fabric 62 is slightly depressed and does not detract from the fixation component's vertical attraction for plate 50. Fabric 62 may be made from a microfiber that has substantially reduced blood transmission characteristics over normal fibers and is washable a large number of times. Fabric 62 may be obtained from Burlington Cloppman and is generically referred to as a microfiber fabric. An example of a suitable microfiber is one that is 99% polyester and 1% carbon fiber. Fabric 62 is attached to plate 50 by a crack and peel tape system or by battens and fixation components. In an alternative embodiment, plate 50 may be coated or treated to achieve the functional benefits of the described fabric. Bridge 56 optionally may be coated with the same textile component or covering.

Fixation Components

The fixation and retraction system 10 also includes fixation components. All of the fixation components contain rare-earth magnets and attach to plate 50 or bridge 56 or to other fixation components. System fixation components work on both bare and draped plates 50 and 56. In designing the fixation components, larger magnets are used for larger elements that, as a consequence of their greater height, have a larger moment arm when a retraction component is attached. Generally, in hand surgery applications, components with more elevated retractor points have correspondingly; larger base magnets to ensure all components have a minimum of about 800 grams of retraction from any point in the system. As shown in FIGS. 1–3, illustrative fixation components include pawn 64, queen 66, rook 68, lance 72, knight 74 (shown only in FIG. 13), arid cam locking base 76.

(a) Magnetic Circuit Design

Figure 7:
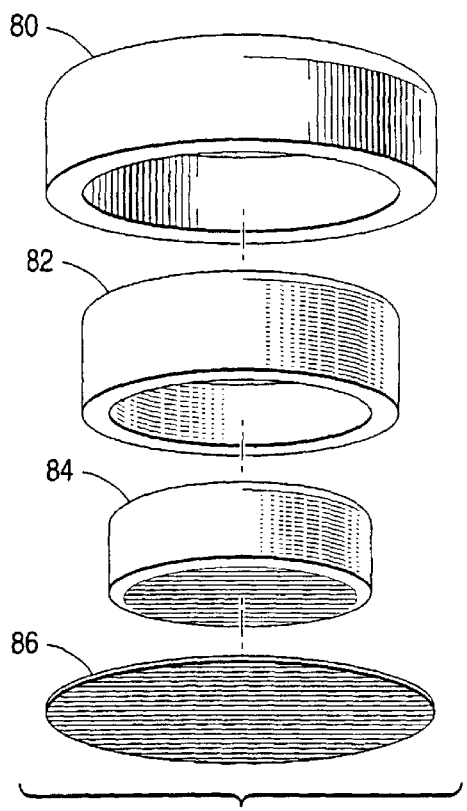
FIG. 7 is an exploded perspective view of the components of the magnetic circuit design of this invention.
Figure 8:
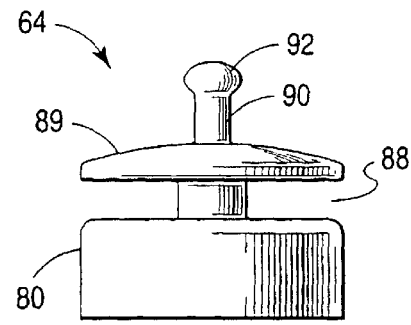
FIG. 8 is a side elevation view of the pawn of this invention.
Figure 9:
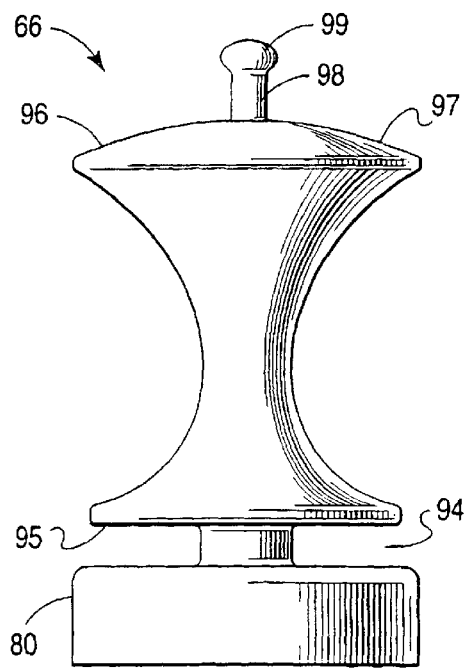
FIG. 9 is a side elevation view of the queen of this invention.

The fixation components may all have a magnetic circuit design utilizing the components shown in FIG. 7, consisting of external housing 80, ferromagnetic cup 82, rare earth magnet 84, and base cap 86. Rare earth magnet 84 (typically a disk or cylindrical section) is housed in ferromagnetic cup 82 (typically, for instance, 12L14 steel), in turn housed in external housing 80, which external housing is a stainless steel (e.g., non-magnetic 304 stainless steel). Base cap 86 (for example, a thin plate of 304 stainless steel) fits over magnet 84 and hermetically seals the magnet 84 and cup 82 within the external housing 80. Housing magnet 84 within ferromagnetic cup 82 focuses the magnetic field so that the magnetic force downward is maximized, while the magnetic force radiated upward is minimized. The narrow waist of queen 66 and rook 68, shown in FIGS. 1 and 2 and further described below, and the cleats, described below, also serve to maximize magnetic force downward and minimize magnetic force radiated upward.

In one embodiment of the magnetic circuit design of this invention, external housing 80 and base cap 86 are both formed from 304 stainless steel, and form a hermetic seal so that rare earth magnet 84 is completely encapsulated within the 304 stainless steel in order to avoid corrosion that may result from steam in the autoclave environment. In this embodiment, ferromagnetic cup 82 may be formed from 12L14 steel. All stainless steel components may be surgical stainless steel.

In some embodiments of this invention, as indicated above, the housing 80 and other structures not including the magnetic cup 82 and the magnet 84, are formed from non-magnetic material. Non-magnetic material includes material, such as copper, aluminum, some stainless steel and other alloys, and most plastics, to which a magnet is not attracted. In a plastic housing 80 embodiment, the plastic may be molded to form a shell encasing the magnet.

(b) Pawn

As shown in FIGS. 1–3 and 8, pawn 64 is a low-profile fixation component having a cleat 88 in the form of a deep annular groove between the external housing 80 and a cap 89. Cleat 88 can grip plate edge 52 or be used as a jam-cleat for an elastic tube, as described below. A boss 90 is positioned on the cap 89 surface and serves as an attachment point for any of the retraction or dynamic components, discussed below. Boss 90 has elliptical nob top 92 that a dynamic component or that retains a retraction component as further described below. Pawn 64 is often used at plate edge 52 or on bridge 56. Its low profile makes it ideal for holding fingers in extension, further described below.

(c) Queen

Queen 66, illustrated in FIGS. 1–3 and 9, is the most versatile fixation component of the system. Queen 66 has a cleat 94, similar in structure to cleat 89 of pawn 64 and likewise enabling queen 66 to grip plate edge 52 or a dynamic component, as explained below. Cleat 94 is defined by external housing 80 and the bottom 95 of queen body 96, a body of revolution having a concave face that curves inward in an hourglass shape, and a dome-shaped top 97. Like pawn 64, queen 66 is topped with a boss 98 with an elliptical nob top 99 that may engage a reaction component or a dynamic component.

(d) Rook

Figure 10:
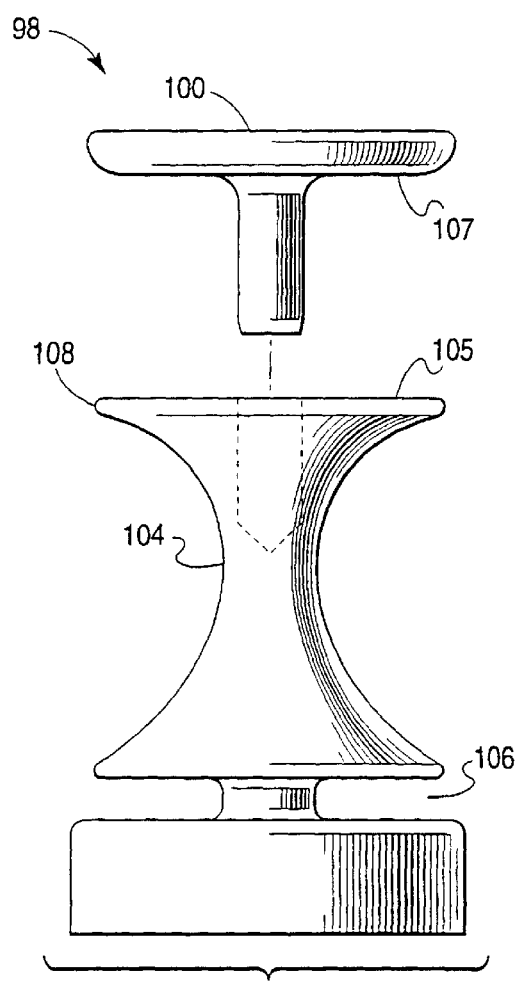
FIG. 10 is an exploded side elevation view of the rook of this invention.

As shown in FIGS. 1–3 and 10, rook 68 resembles queen 66, except that body 108, which has a narrow waist 104, is symmetrical and has a flat top 105. As shown in FIG. 10, flat head 100 positioned above rook body 108 has a generally flat underside 107 spaced above flat top 105 to define a cleat 106. The flat top surface of head 100 can receive a pawn 64 or queen 66 and thereby acting as a riser for pawn 64 or queen 66, providing a higher retraction angle, as shown in FIGS. 1 and 3. Four rooks 68 magnetically attached under plate 50 can serve as feet, as illustrated in FIG. 1. Rook 68 has cleats 106 at both top and bottom, allowing it to grip plate edge 52 or secure fingers with a dynamic component. Rook 68 may be made in a two-part design with head 100 press fit into rook body 108, as shown in FIG. 10. In one embodiment, head 100 is ferromagnetic 416 stainless steel and body 108 is non-magnetic 304 stainless steel. Ferromagnetic head 100 allows stable and effective stacking of components, as shown in FIG. 3.

(e) Cam Locking Base

Cam locking base 76, illustrated in FIGS. 1, 2, and 11, creates the support for a second surgical fixation level, such as bridge 56, discussed above, and provides a base for lance 72, discussed below. As shown in FIG. 2, bridge legs 58 are formed by folding each end of bridge 56 downward at 90° angles. As shown in FIG. 2, legs 58 of bridge 56 are received in a slot 127 in cam locking base 76. Rotating cam shaft 128 with loop 129 forces cam surface 126 against one face of leg 58, thereby securing it in slot 127 in cam locking base 76. Numerous other locking mechanisms can also be used, such as a thumb screw, a spring clip, and other mechanical locks.

Base 76 also has recess 114 for receiving lance 72, discussed below.

(f) Lance

Lance 72, shown in FIGS. 1, 2, and 12, is a rod that fits into recess 114 (shown in FIG. 11) in the top of cam locking base 76 and to which other components may attach. Lance 72 has boss 116 and diameter 118 of shaft 120 of lance 72 is such as to allow any of the retraction components to slide up and down through larger width of cutout 138, described below, and to engage shaft 120 when shaft 120 is forced into smaller width of cutout 138, described below.

The combination of base 76 and lance 72, as shown in FIG. 1, allows high-angle retraction using boss 116. The height provided by the combination of base 76 and lance 72 allows a hand to be placed on its side for a surgical procedure, for example, so that the combination of base 76 and lance 72 acts as an infinitely height-adjustable retractor anchor. Boss 116 on top end 121 of lance 72 may attach to a retraction component, such as four prong retractor 134, or end 158, or a dynamic component, such as elastic tube 160, discussed below.

As can be seen in FIG. 1, shaft 120 of lance 72 fits through the cutout 138 of retraction component end 158, slightly deforming cutout 138 and creating a secure fit. Thus, lance 72 may engage a retraction component, such as four prong retractor 134 or end 158, anywhere along the height of shaft 120 of lance 72.

(g) Knight

Knight 74, illustrated in FIG. 13, has base 122 that houses a magnet and cleat 123 that will anchor elastic tubes, discussed below, and that can also grip plate edge 52. Knight 74 also has boss 124 on top of shaft 125. Knight 74 functions similar to the combination of lance 72 and cam locking base 76. Similar to lance 72, the diameter of shaft 125 is such as to allow any of the retraction components to slide up and down through larger width of cutout 138, described below, and to lock to shaft 125 when shaft 125 is forced into smaller width of cutout 138, described below. Knight 74 also allows high-angle retraction using boss 124. The height provided by knight 74 allows a hand to be placed on its side for a surgical procedure, for example. Boss 124 of knight 74 may attach to a retraction component, such as four prong retractor 134, or end 158, or a dynamic component, such as elastic tube 160, discussed below.

Retraction Components

Figure 14:
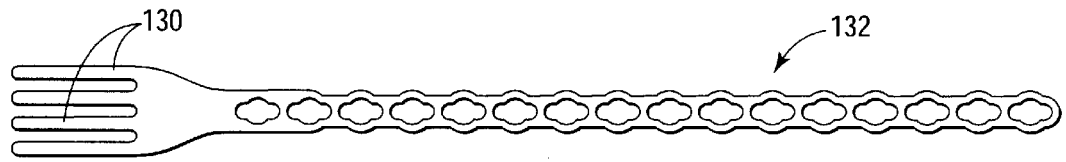
FIG. 14 is a top plan view of a flat blank of a four prong, blunt retraction component of this invention.
Figure 16:
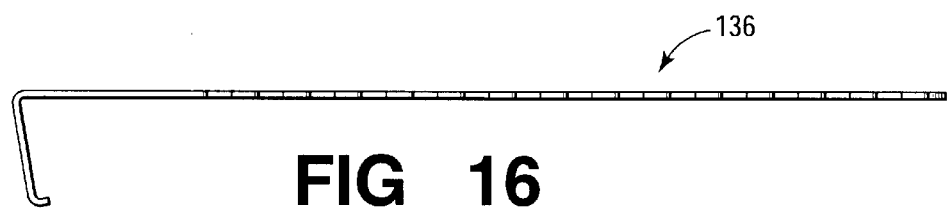
FIG. 16 is a side elevation view of the retraction component of FIG. 15.
Figure 17:
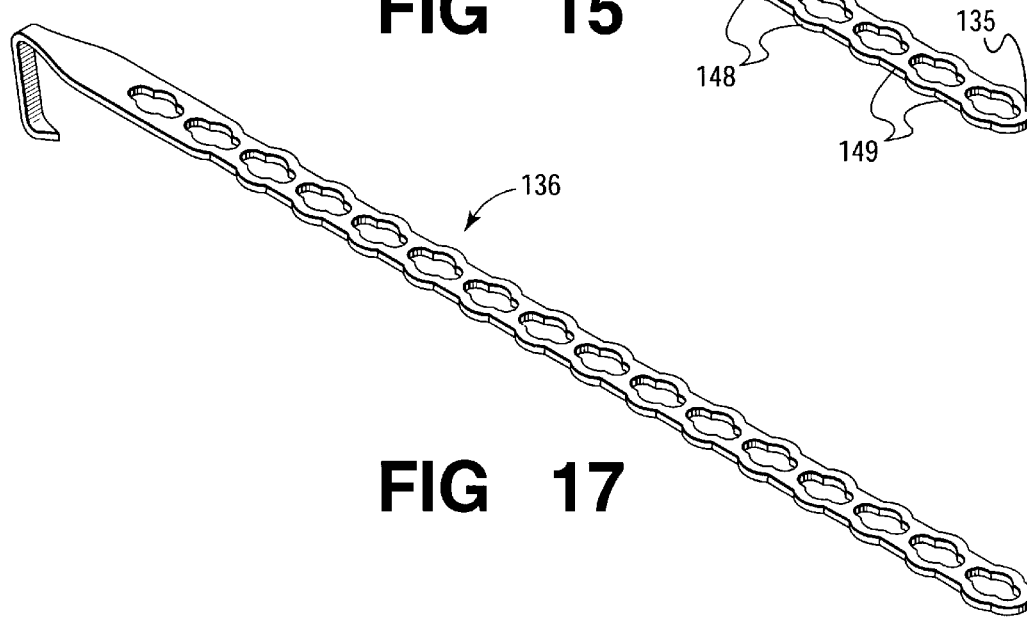
FIG. 17 is a perspective view of a fang of this invention.

The retraction components of system 10 are light, thin, economical instruments that perform their coupling function with minimal clutter while providing superb control and feel. The retraction components are typically 0.020 inch thick stainless steel, which is and autoclavable to 300° F., although other materials could also be used. The retractors have between one and six blunt, flexible hooks or prongs 130. The length of prong 130 may be increased in proportion to the number of prongs to provide progressively deeper reach. FIG. 14 shows flat blank 132, usable to form four prong blunt retraction component 134, shown in FIGS. 1, 3, 15 and 16. Various other retraction components with one, two, three, five, and six or more prong blunt ends may also be utilized. As shown in FIG. 17, a sharp, single-prong retractor, in the form of fang 136 may be used for skin piercing and wound edge reduction.

Figure 15:
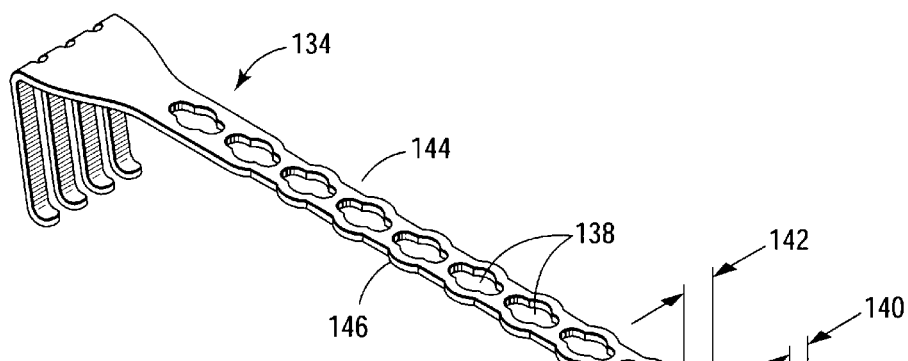
FIG. 15 is a perspective view of a four prong, blunt retraction component of this invention.

Retractors 134, 136, 150, 152, all share the same system arm design of repeating interlocks and key-holes. As shown in FIG. 15, for example, an elongated arm 144 is a strip of sheet metal perforated by a series of double-keyhole shaped cutouts 138 having at least two different widths 140 and 142.

The "double key-hole" 138 could also be described as an oblong opening centered on a round hole having a diameter larger than the oblong width but smaller than its length. As shown in FIGS. 1 and 3, boss 98 of queen 66 can pass through larger width or diameter 142 of cutout 138, but not through smaller width 140. Boss 90 of pawn 64 and boss 116 of lance 72 are the same size as boss 98 of queen 66, and those can be received in cutouts 138 and connect with the retraction components in the same manner. This allows retractors 134, 136, 150, 152 to attach to: (a) bosses 90, 98, 116 of the system 10 fixation components, (b) elastic tubes, (c) lance 72, or (d) each other. Using 0.020 inch sheet metal for retractors 134, 136, 150, 152, provides flexibility and a sufficiently constant bend modulus to allow them to be cut or bent to form specialized instruments. For instance, the end 135 of a retractor, such as four-prong retractor 134, may be bent so that it attaches directly to edge 52 of plate 50.

As illustrated in FIGS. 1 and 15, the longitudinal outer edges 146 of retractor 134 arm 144 undulate, alternating wider regions 148 with narrower regions 149. Cutouts 138 are long enough to accommodate the wider regions 148 of arms 144, but cutouts 138 are wide enough at portion 142 to accommodate only the narrower portion 149 of arm 144. This makes it possible to pass an arm 144 through key-hole shaped cutout 138 and then rotate it 90 degrees to lock the two arms together. Retractors 136, 150 and 152 generally have the same arm 144 configuration as retractor 134. In an alternative embodiment of arm 144, edge 146 of arm 144 is linear, with single keyhole shaped cutouts.

Extender component 150, shown in FIG. 18, is essentially arm 144 without prong 130, and interlocks extender 150 with other retraction components to create extended retraction element 152. Extender 150 and arms 144 of retractors 134, 136, 150, 152 are sized so that the elastic tube 160 can be slid over a portion of extender 150 and thereby attached to extender 150, forming a combination elastic tube and retraction component, as shown in FIG. 1. Extender 150 may also be threaded with elastic tube 160 by threading the tubing in and out of successive apertures, creating a self-locking tourniquet component.

FIGS. 1 and 19 show retraction extension end 158, which telescopingly engages an elastic component, described below. End 158 attaches to any of bosses 90, 98, 116, or 124. End 158 is a short section of extender 150.

A special retraction component, "slim jim" 154, is shown in FIG. 20, and is a user formable retraction component that allows the surgeon to make special retraction components or extenders for standard retractors. Slim-jim 154 is formed using 0.020 inch sheet metal and is narrower than arm 144. Thus, it is useful when a retraction component having a narrow arm is required. The surgeon may form slim jim 154 into a desired shape using standard hemostats.

FIG. 21 shows scalpel handle holder 156, which attaches to a scalpel handle in place of a traditional scalpel blade, forming a handle for retraction.

As shown in FIG. 3, one or more prongs 130 on the retraction components, such as four-prong retractor 134, may hook an area of skin to be retracted. If the retractor is fang 136, it will penetrate the skin. Four-prong retractor 134 or fang 136 is then pulled into position, so that the wound is opened. Arm 144 of four-prong retractor 134 is attached to a fixation component, queen 66, which magnetically adheres to plate 50 (not shown in FIG. 3), so that the retractive position is secured.

Dynamic Components

The dynamic components of system 10 include elastic tube 160, shown in FIGS. 1–3. The elastic tube 160 can be made from any suitable elastic material, including, without limitation, latex rubber, silicone rubber and materials of similar elasticity. In one embodiment, the elastic tubing has a 0.125 inch internal diameter with a Poison ratio and durometer that provide a secure mechanical lock onto a cleat. Elastic tube 160 increases in diameter when compressed and decreases in diameter when stretched. Elastic component 160 can be disposable and may have an 8:1 stretch modulus. These inherent qualities makes it easy to slide onto a boss or retractor arm and yet lock them in position under tension.

All of the fixation components and retraction components of system 10 have the ability to grip elastic tubes 160. Elastic tube 160 is flexible to allow linear pull on an incision area even when pulling around objects. The cleat 88, 94, 106, 112, on all fixation components makes it easy to attach and adjust the free end of elastic tube 160 by winding a portion of elastic tube 160 into the groove. A half turn will secure, and a full turn will lock, elastic tube 160 in place in cleat 88, 94, 106, 123. Elastic tube 160 attaches to cleat 88 of pawn 64 by wrapping around the shaft of cleat 88, as shown in FIG. 3. Queen 66, rook 68 and knight 74 also have cleat that tether elastic tube 160 in the same manner. Any of bosses 90, 98, 116 or 124 may engage elastic tube 160. As shown in FIG. 1, for example, boss 90 of pawn 64 engages elastic tube 160, while second end of elastic tube 160 is telescopingly engaged to a retraction component.

Sterilization Tray

Figure 22:
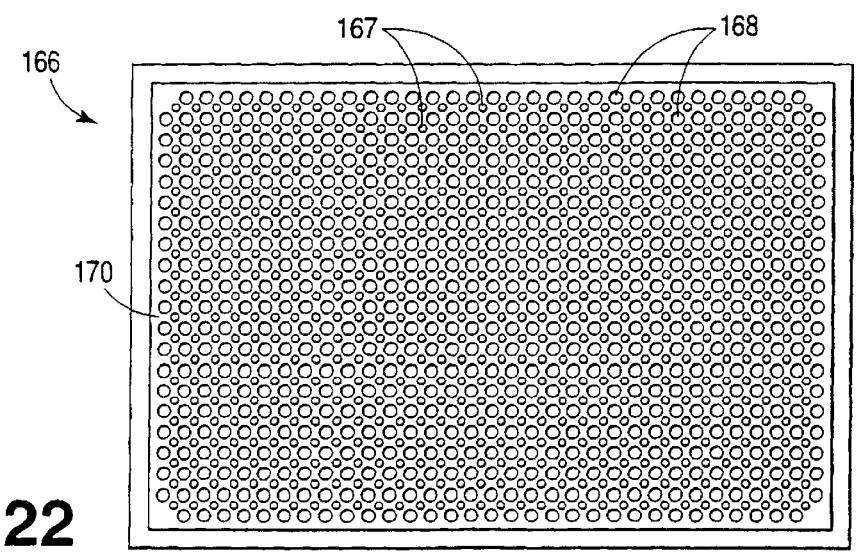
FIG. 22 is a top plan view of a sterilization tray of this invention.

A sterilization tray 166, shown in FIG. 22, may be made of ferromagnetic stainless steel or other suitable material and is generally about one half the size of plate 50. Fixation and retraction components are loaded onto tray 166 and then way 166 and the components are autoclaved. Tray 166 contains a plurality of raised protrusions or knobs 167 and holes 168 on tray plate 170. Fixation components, such as pawn 64, are hold by magnetic attractions and rest on knobs 167, minimizing contact with tray 166 and thereby permitting good circulation of steam through holes 168 and around all surfaces of paw 64 and other system 10 components. Tray 166 is a single sheet with four sides 169, forming a pan-shape. The trays may be stacked during autoclaving or storage, as shown in FIG. 23. Comb-like polymeric strips having pegs that are received in holes 168 can hold retractors during the autoclaving cycle. Such comb-like strips are available for use in commercially available autoclave trays.

System Utilization

The system components can be used together to create surgical solutions. All of the components of system 10 may be used in a variety of combinations and mechanical and magnetic arrangements to achieve the requirements of a particular surgical procedure. For example, in a hand surgery embodiment, system components stack to create high-rise fixative points up to on the order of three inches tall extending to approximately six inches tall when combined with bridge 56. Similarly, an inclinable table may be created. Rooks 68 can be used as feet either individually or stacked to create an inclined surface. Rooks also stack to create effective palm grips, which allows fingers to be stabilized in a fist configuration.

The same components may have retractors attached for static retraction, which is retraction that is constant for a given retractor position. Dynamic retraction is achieved by applying elastic tubes to retractor tips and anchoring the elastic tubes to a static base. Such dynamic retraction can maintain a nearly constant force over a retractive range. For example, as a surgeon deepens an incision it is simultaneously further retracted. In short, unlike static retraction, it maintains a nearly constant force as an incision opens. This is ideal for incision retraction requiring repositioning or minor manipulation. In both cases, the retractor anchors can be moved as required.

The components may also be used as trapping mechanisms. Narrow waist 104 allows a series of rooks 68 or queens 66 to be used to make "finger grippers," shown in FIG. 24, by placing one component on either side of a finger, holding it in place. In addition, either cleat 106 of rook 68 allows elastic tube 160 to bind one or two fingers, as shown in FIG. 25.

System 10 components also combine to form various anchor elements. For instance, among many other alternatives, solid anchor points may be created by combining edge-locked pawn 64 and queen 66. Two queens 66 may be combined to provide an anchor, with each queen 66 locked to a single retraction component. Components with top bosses 90, 98, 116, or 124 will accommodate two retractors 134, 136, 150, 152, plus a dynamic retractor in each cleat, and retraction components, such as four-prong retractor 134, and extenders 150 may lock together to increase reach as shown in FIG. 1. Two queens 66 may be placed on either side of a wrist or other limb and used to trap a tourniquet in place. One or two queens 66 or rooks 68 may hold the wrist in place.

This fixation and retraction system 10 is highly compatible with conventional components, which adapt easily to the system. For example, hemostats may be attached using elastic tubes by threading one end of an elastic tube through a finger hole opening on a hemostat and binding the other end of the elastic tube to a cleat on a fixation component. The hemostat may then be used to clamp an object while the fixation component provides the fixation and retraction required by holding the hemostat in place.

Utilization of Film

FIG. 26 shoves another embodiment of the magnetic fixation system attaching latex material such as latex glove 174 to plate 50. Elastic film may be used to enrobe anatomical members to immobilize them and maintain sterility in the surgical field. For instance, as shown in FIG. 26, a latex glove 174 covers the patient's hand after it has been sterilized and prepared for surgery. FIG. 26 shows glove 174 covering one finger 176. Each tip of each finger of glove 174 may be elongated and fixed against plate 50 with a fixative component such as rook 68 or queen 66. Stretching fingers of glove 174 causes them to grip the patient's fingers. This process is repeated until all required sections of the glove are secured to the surface. This embodiment of the fixation system provides medical personnel additional assurance that hard to sterilize fingernail beds or other anatomical areas are effectively isolated from adjacent surgical fields on the hand. Surgery is performed simply by cutting open a section of the secured glove and exposing the surgical area.

Portions of specifically designed latex or other types of film gloves or may be reinforced to strengthen the glove and resist tearing by making portions of the glove thicker. This can be accomplished, for instance, by forming an annular depression in the finger-forming position of the glove mold, thereby creating a thickened ring at the location of the depression in the glove finger.

Surgical Drape Fixation

Figure 27:
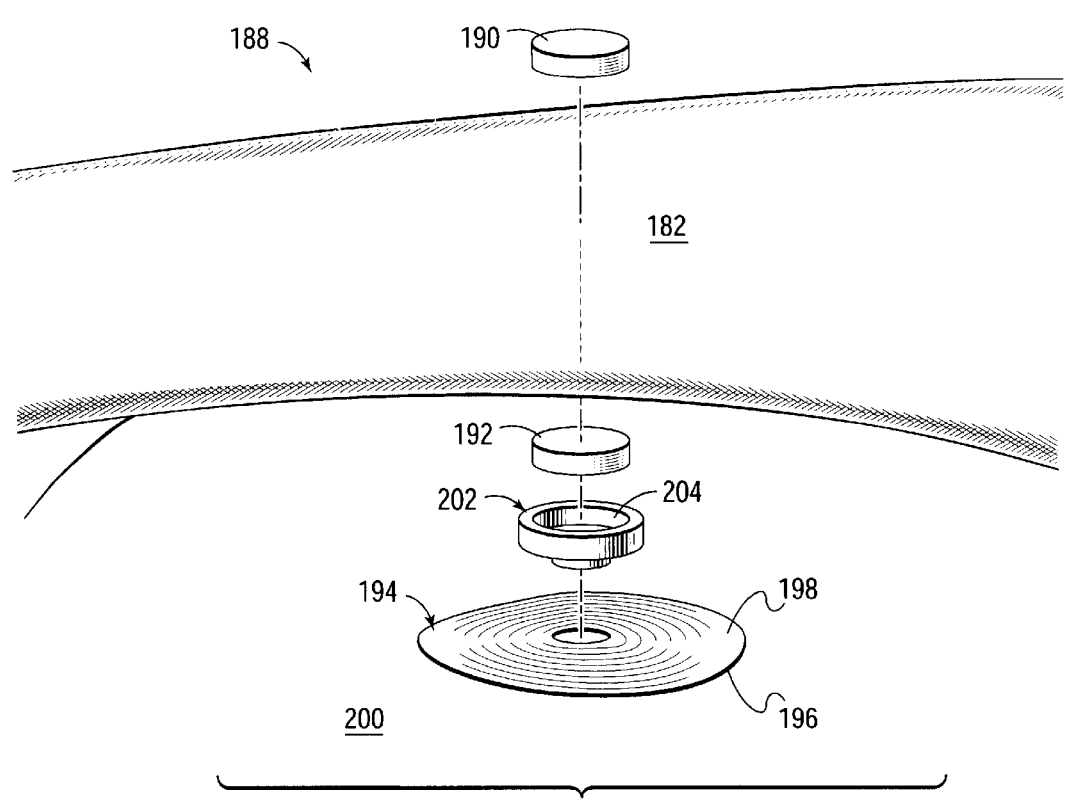
FIG. 27 is an exploded perspective view of a method and system for active fixation of a magnet fixation system.

FIG. 27 shows a perspective view of active fixation of drape fixation system 188. Active fixation is the attraction between two magnets and provides for a strong attraction that is polarity dependent. Active fixation is used in minimal clearance circumstances where the surgical drape is to be held in close proximity to the operative site and a low profile fixation system is required.

Magnets 190, 192, shown in FIG. 27, are preferably rare earth magnets, as described above. Skin fixation tape is made by several manufacturers. For example, 3M makes a skin securing tape usable for the fixation tape 194 sold under the product name Tegaderm. Smith & Nephew also sells skin fixation tape under the product name Hypafix. Preferably, the skin securing tape has properties similar to skin securing tape used to attach electrodes to a body. In an alternative embodiment, magnets either covered with an inactive finish or ones with non-reactive properties may be attached to the skin using adhesive or double sided foam adhesive.

As shown in FIG. 27, drape fixation system 188 of this invention holds a material such as surgical drape 182 in place without puncturing the membrane of drape 182. Magnets 190, 192 secure surgical drape 182 to a patient providing fail safe fluid protection. Fixation tape 194 has first side 196 and second side 198. First side 196 of fixation tape 194 adheres to skin surface 200.

Second magnet 192 mounts within metal cup 202 in cavity 204, which is sized to receive it. Attraction of magnet 192 for cup 202 holds magnet 192 in place, but it may be further secured with an appropriate adhesive. Cup 202 may attach to fixation tape 194 with a snap connector. In an alternative embodiment, magnetic attraction between metal cup 202 and fixation tape 194 provide the locking mechanism for securing drape fixation system 188 in position.

Surgical drape 182 is positioned between magnets 190, 192 and is secured when magnet 192 locks into position on fixation tape 194. Medical personnel may place a sufficient number of drape fixation systems 188 around a patient to protect the patient during a medical procedure.

Figure 28:
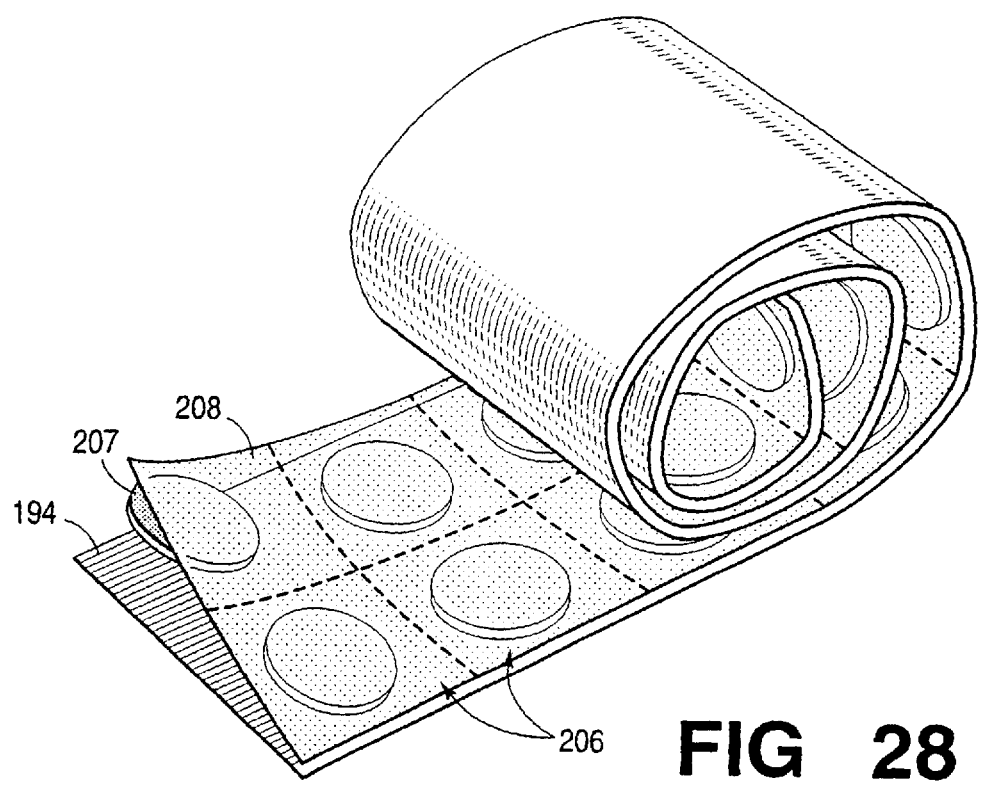
FIG. 28 is a perspective view of a fixation tape system.

As shown in FIG. 28, fixation tape system 188 can be manufactured in a manner such that a plurality of fixation tape units 206 are removably connected in a roll-up configuration. In this configuration, each individual fixation tape unit 206 can be torn away from the roll and used as needed. Each fixation tape unit 206 includes magnet 207, fixation tape 194, and cover 208. Magnet 207 is disposed between fixation tape 194 and cover 208. Preferably, magnet 207 is formed in a flat disc shape.

Figure 29:
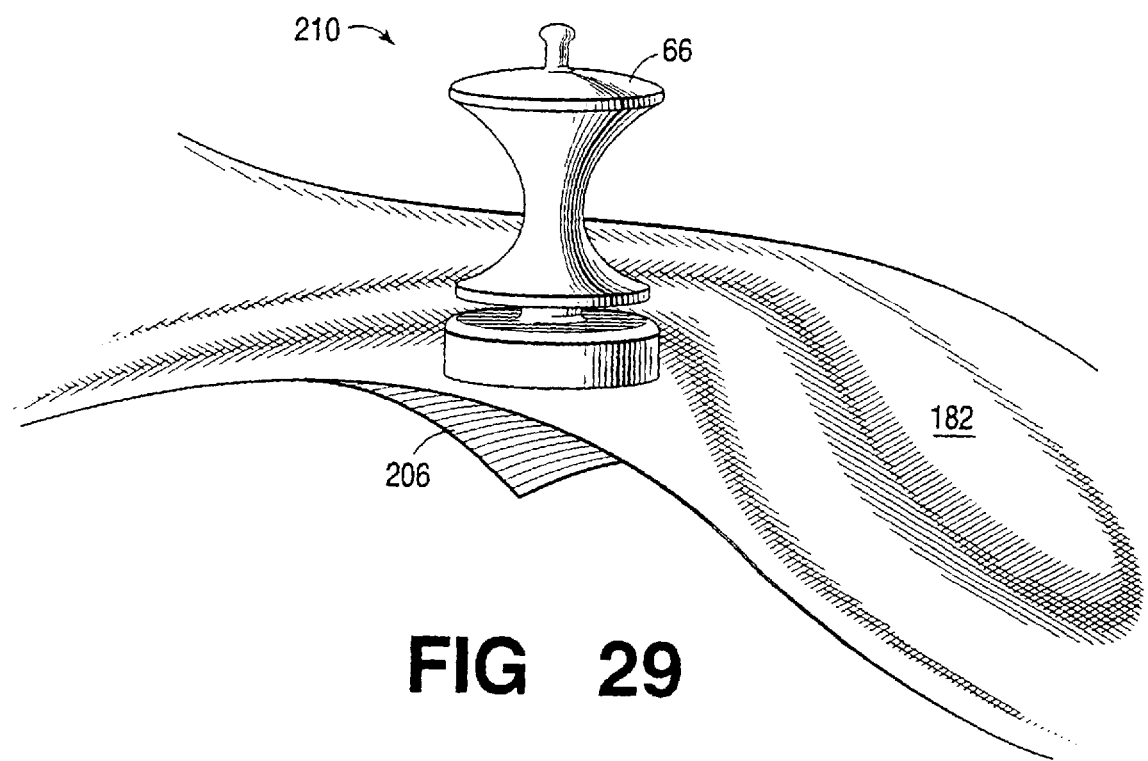
FIG. 29 is a perspective view of a method and system for passve fixation of the magnetic fixation system of this invention.

FIG. 29 shows passive fixation system 210, an alternative embodiment of the drape fixation system. Passive fixation is the attraction between a magnet and magnetic material. This attraction is independent of magnetic pole orientation. Passive fixation is used where adequate clearance is available to allow the use of metal cups which provide far greater force and the additional advantage of a closed magnetic loop minimizing magnetic fields.

Passive fixation system 210 includes a fixative component, such as queen 66, surgical drape 182 and fixation tape unit 206. An alternative embodiment of passive fixation system 210 utilizes disposable elements packaged in a sterile condition and used only once. Tape unit 206 include a metal plate or other ferromagnetic material that may be temporally affixed to the patient with adhesive and that is strongly attracted to queen 66. Fixation may be provided by fixation tape unit 206 or by adhesive. Surgical drape 182 is removably dispose between queen 66 and fixation tape unit 206. Attraction occurs from queen 66 and the metal plate of fixation tape unit 210.

Any number of accessories may be included with drape fixation system 188 or 210. Accessories may include, for example, tubes, cannulas, intravenous shunts, airways or electronic monitoring systems. In addition, strain from other apparatus can be relieved using an accessory with fixation system 188 or 210. An accessory such as a tube is connected to the magnet. Any number of connection methods may be used including adhesive tape or another magnet combination.

The fixation system of this invention is not confined to the embodiments described herein but includes variations and modifications within the scope and spirit of the foregoing description, the accompanying drawings, and the following claims. The components may be sized to accommodate a particular surgical procedure. For example, larger versions of the components described herein may be used for various types of surgery, including human craniofacial and orthopedic surgery. Additionally, numerous modifications in the shape and size of the described fixation components can be made in order to adapt the principals of this invention to the anatomical and other requirements of surgical procedures on humans in addition to hand surgery and veterinary surgical procedures of all kinds.

We claim:

1. A system for use in fixation comprising a magnet respositionably attachable to a base component in an indeterminate location for linking tissue to the base component during a surgical procedure.

2. The system of claim 1, further comprising a fixation component.

3. The system of claim 2, further comprising a boss on the fixation component.

4. The system of claim 2, wherein the fixation component has a first face, and magnetic flux associated with the magnet is focused on the first face.

5. The system of claim 2, wherein the fixation component further comprises at least one cleat.

6. The system of claim 1, further comprising a stainless steel plate.

7. The system of claim 6, wherein the plate is generally rectangular.

8. The system of claim 1, further comprising a coupling component.

9. The system of claim 8, wherein the coupling component comprises at least one prong.

10. The system of claim 9, wherein the at least one prong is blunt.

11. The system of claim 9, wherein the at least one prong is sharp.

12. The system of claim 8, wherein the coupling component comprises an arm having at least one aperture.

13. The system of claim 1, further comprising elastic tubing.

14. The system of claim 13, wherein the elastic tubing comprises at least one silicone rubber tube.

15. The system of claim 1, wherein the magnet comprises a rare earth magnet.

16. The system of claim 15, wherein the magnet comprises somarium cobalt.

17. The system of claim 15, wherein the magnet comprises neodymium.

18. The system of claim 15, wherein the magnet is disk shaped.

19. The system of claim 1, further comprising a sterilization tray.

20. The system of claim 19, wherein the tray comprises a metal plate perforated with a plurality of holes.

21. The system of claim 19, wherein the tray comprises a metal plate having a plurality of protrusions.

22. The system of claim 19, wherein the tray comprises four sides.

23. A system for use in fixation comprising: a magnet for mechanically linking tissue to a base component during a surgical procedure; and a fixation component, wherein the fixation component comprises a non-magnetic housing and a ferromagnetic cup.

24. The system of claim 23, further comprising a base cap and wherein the housing and the base cap are formed of stainless steel.

25. The system of claim 24, wherein the housing and the base cap form a hermetic seal around the magnet.

26. The system of claim 23, wherein the magnet is contained in the ferromagnetic cup and the ferromagnetic cup is contained in the housing.

27. The system of claim 23, wherein the ferromagnetic cup is formed of stainless steel.

28. A system for use in fixation comprising: a magnet for mechanically linking tissue to a base component during a surgical procedure; and a fixation component, wherein the fixation component further comprises a body having narrow waist.

29. A system for use in fixation comprising: a magnet for mechanically linking tissue to a base component during a surgical procedure; and a stainless steel plate, wherein instructions for use of the system are indelibly affixed to the plate.

30. The system of claim 29, wherein the instructions are indelibly affixed by laser etching the instructions on the plate.

31. A system for use in fixation comprising: a magnet for mechanically linking tissue to a base component during a surgical procedure; and a stainless steel plate, wherein the plate is generally crescent-shaped.

32. A system for use in fixation comprising: a magnet for mechanically linking tissue to a base component during a surgical procedure; and a stainless steel plate, further comprising a fabric covering at least a portion of the plate.

33. The system of claim 32, wherein the fabric is a microfiber.

34. A system for use in fixation comprising: a magnet for mechanically linking tissue to a base component during a surgical procedure; and a stainless steel plate, wherein the plate is treated to reduce friction between the plate and the magnet.

35. A system for use in fixation comprising: a magnet for mechanically linking tissue to a base component during a surgical procedure; a coupling component comprising an arm having at least one aperture, wherein the at least one aperture has at least two widths.

36. A system for use in fixation comprising:
a magnet for mechanically linking tissue to a base component during a surgical procedure, a housing and
a ferromagnetic cup.

37. The system of claim 36, wherein the housing comprises a recess within which the magnet is positioned and a base cap for sealing the magnet within the housing.

38. A device for repositionably securing a structure in a desired position during surgery, comprising a magnet repositionably attachable to a base component in an indeterminate location and a coupling component for coupling the structure to the base component.

39. The device of claim 38, further comprising:
a fixation component;
a silicone rubber tube; and
a ferromagnetic base plate.

40. The device of claim 39, wherein the fixation component magnetically adheres to the plate.

41. The device of claim 38, wherein the coupling component comprises an elongated member.

42. A device for repositionably securing a structure in a desired position during surgery, comprising:
a magnet,
coupling component for coupling the structure to a base component,
a fixation component comprising a base within which the magnet is housed, a body attached to the base, and a boss on the body
a silicone rubber tube; and
a ferromagnetic base plate.

43. The device of claim 42, wherein the boss is adapted to receive an end of the silicone rubber tube.

44. A device for repositionably securing a structure in a desired position during surgery, comprising a magnet and a coupling component for coupling the structure to a base component, the coupling component comprising an elongated member comprising at least one keyhole shaped aperture and undulating opposed edges.

45. The device of claim 44, wherein the at least one aperture has a first width and a second width.

46. The device of claim 45, wherein the second width is adapted to receive a boss on the fixation component to couple the elongated member to the fixation component.

47. A device for repositionably securing a structure in a desired position during surgery, comprising a magnet and a coupling component for coupling the structure to a base component, the coupling component comprising an elongated member comprising a thin, perforated member of uniform thickness and varying width.

48. A device for repositionably securing a structure in a desired position during surgery, comprising a magnet and a coupling component for coupling the structure to a base component, the coupling component comprising an elongated member thatterminates in at least one prong.

49. The device of claim 48, wherein the at least one prong is blunt.

50. The device of claim 48, wherein the at least one prong is sharp.

51. The device of claim 48, wherein the at least one prong comprises a plurality of blunt prongs.

52. A surgical fixation system, comprising:
a ferromagnetic base plate, and
a fixation component comprising a magnet repositionably attachable to the base in an indeterminate location.

53. The surgical fixation system of claim 52, wherein the fixation component further comprises a housing for the magnet.

54. The surgical fixation system of claim 53, further comprising a cap enclosing the magnet within the housing.

55. The surgical fixation system of claim 52, further comprising a boss attached to the magnet.

56. The surgical fixation system of claim 52, further comprising a housing for the magnet and a boss attached to the housing.

57. The surgical fixation system of claim 52, further comprising a housing for the magnet and a body attached to the housing.

58. The surgical fixation system of claim 37, further comprising a boss attached to the body.

59. The surgical fixation system of claim 52, further comprising a body attached to the magnet and having a flat top surface.

60. The surgical fixation system of claim 59, further comprising at least one cleat.

61. The surgical fixation system of claim 52, further comprising a body attached to the magnet having a post.

62. A surgical fixation system, comprising:
a ferromagnetic base plate, and
a fixation component comprising a magnet repositionably attachable to the base, wherein instructions for use of the system are indelibly affixed to the base plate.

63. A surgical fixation system, comprising:
a ferromagnetic base plate, and
a fixation component comprising a magnet repositionably attachable to the base, a housing for the magnet, and a ferromagnetic cup within which the magnet is positioned.

64. A surgical fixation system, comprising:
a ferromagnetic base plate, and
a fixation component comprising a magnet repositionably attachable to the base, wherein the fixation component further comprises a housing for the magnet and a cap enclosing the magnet within the, wherein the cap hermetically seals the magnet within the housing.

65. A surgical fixation system, comprising:
a ferromagnetic base plate, and
a fixation component comprising a magnet repositionably attachable to the base, at least one cleat and a flux focusing housing for the magnet.

66. The surgical fixation system of claim 65, further comprising a ferromagnetic cup within the housing.

67. The surgical fixation system of claim 65, further comprising a cap enclosing the magnet within the housing.

68. The surgical fixation system of claim 67, wherein the cap and the housing form a hermetic seal.

69. A surgical fixation system, comprising:
a ferromagnetic base plate,
a fixation component comprising a magnet repositionably attachable to the base, and two cleats attached to the magnet.

70. A surgical fixation system, comprising:
a ferromagnetic base plate,
a fixation component comprising a magnet repositionably attachable to the base, a body attached to the magnet, a boss attached to the body, and two cleats adjacent to the body.

71. A surgical fixation system, comprising:
a ferromagnetic base plate, and
a fixation component comprising a magnet repositionably attachable to the base, a body attached to the magnet having a post and a boss on the top of the post.

72. A surgical fixation system, comprising:
a ferromagnetic base plate, and
a fixation component comprising a magnet repositionably attachable to the base and a locking base attached to the magnet.

73. A fixation component for use with a ferromagnetic component, the fixation component comprising:
a magnet;
a housing for the magnet; and
a cleat attached to the housing.

74. The fixation component of claim 73, further comprising a boss attached to the housing and to which another component can be attached.

75. The fixation component of claim 73, further comprising a second cleat and a boss attached to the housing and to which another component can be attached.

76. The fixation component of claim 73, further comprising a flat surface to which a second magnet can be attached.

77. The fixation component of claim 73, further comprising a socket within which a post can be positioned.

78. The fixation component of claim 73, further comprising a body attached to the housing, the body having a narrow waist between two flared regions.

79. The fixation component of claim 78, further comprising a boss attached to the body.

80. The fixation component of claim 79, the boss comprising a shank having two ends, one of which is attached to the body and the other of which attaches to a conical cap.

81. The fixation component of claim 73, further comprising a coupling component comprising an elongated member perforated with key-hole shaped apertures and having undulating opposed edges.

82. The fixation component of claim 73, further comprising a coupling component comprising a thin, perforated, elongated member of uniform thickness and varying width.

83. The fixation component of claim 82, wherein the elongated member terminates in at least one prong.

84. The fixation component of claim 83, wherein the at least one prong is blunt.

85. The fixation component of claim 83, wherein the at least one prong is sharp.

86. The fixation component of claim 83, wherein the at least one prong comprises a plurality of blunt prongs.

87. The fixation component of claim 73, further comprising elastic tubing for coupling to the fixation member.

88. The fixation component of claim 73, further comprising an elastic film for enrobing an anatomical member and attachment to a fixation member.

89. The fixation component of claim 73, further comprising a surgical drape secured by the magnet to the base.

90. A method for stabilizing or retracting an anatomical member during surgery comprising:
   (a) coupling a magnet to the anatomical member; and
   (b) attaching the magnet to a ferromagnetic base plate in an indeterminate location.

91. The method of claim 90, wherein the magnet is housed in a fixation component.

92. A method for stabilizing or retracting an anatomical member during surgery comprising:
   (a) coupling a magnet to the anatomical member by coupling to the magnet an elongated member having two ends, key-hole shaped apertures and at least one prong on one end; and
   (b) attaching the magnet to a ferromagnetic base plate.

93. The method of claim 92, wherein the at least one prong engages a portion of the anatomical member.

94. The method of claim 92, wherein the at least one prong is blunt.

95. The method of claim 92, wherein the at least one prong is sharp.

96. The method of claim 92, wherein the at least one prong comprises a plurality of blunt prongs.

97. The method of claim 92, wherein the coupling the magnet to the elongated member is accomplished using elastic tubing.

98. The method of claim 97, wherein the elastic tubing comprises silicone rubber tubing.

99. The method of claim 92, wherein the coupling the magnet to the elongated member is accomplished using a second elongated member having key-hole shaped apertures.

100. A method for stabilizing or retracting an anatomical member during surgery comprising:
   (a) coupling a magnet to the anatomical member; and
   (b) attaching the magnet to a ferromagnetic base plate, wherein the magnet is housed in a fixation component comprising at least one cleat.

101. The method of claim 91, wherein the fixation component further comprises a boss.

102. The method of claim 101, wherein the boss is adapted to receive an end of an elastic tube.

103. The method of claim 102, wherein the elastic tube comprises silicone rubber.

104. A system for use in surgical fixation comprising:
   (a) a magnet; and
   (b) a surgical retractor comprising a hook attached to an elongated member perforated by a series of holes wherein at least one hole comprises at least first and second diameters wherein the second diameter is greater than the first diameter.

\* \* \* \* \*